United States Patent
Xu

(10) Patent No.: US 11,298,029 B2
(45) Date of Patent: Apr. 12, 2022

(54) BLOOD PRESSURE MEASURING APPARATUS, BLOOD PRESSURE MEASURING METHOD, ELECTRONIC DEVICE, AND COMPUTER READABLE STORAGE MEDIUM

(71) Applicant: BOE TECHNOLOGY GROUP CO., LTD., Beijing (CN)

(72) Inventor: Zhihong Xu, Beijing (CN)

(73) Assignee: BOE TECHNOLOGY GROUP CO., LTD., Beijing (CN)

(*) Notice: Subject to any disclaimer, the term of this patent is extended or adjusted under 35 U.S.C. 154(b) by 294 days.

(21) Appl. No.: 16/489,696

(22) PCT Filed: Jan. 31, 2019

(86) PCT No.: PCT/CN2019/074215
§ 371 (c)(1),
(2) Date: Aug. 28, 2019

(87) PCT Pub. No.: WO2020/007041
PCT Pub. Date: Jan. 9, 2020

(65) Prior Publication Data
US 2021/0330203 A1    Oct. 28, 2021

(30) Foreign Application Priority Data
Jul. 3, 2018 (CN) .......... 201810716583.6

(51) Int. Cl.
*A61B 5/021* (2006.01)
*A61B 5/145* (2006.01)
(Continued)

(52) U.S. Cl.
CPC ........ *A61B 5/02125* (2013.01); *A61B 5/0205* (2013.01); *A61B 5/14542* (2013.01);
(Continued)

(58) Field of Classification Search
CPC . A61B 5/02125; A61B 5/7267; A61B 5/0205; A61B 5/14542; A61B 5/318; A61B 2560/02
See application file for complete search history.

(56) References Cited

U.S. PATENT DOCUMENTS

2009/0018422 A1* 1/2009 Banet ............... A61B 5/02125
600/324
2010/0081946 A1* 4/2010 Garudadri ........... A61B 5/0028
600/485
(Continued)

FOREIGN PATENT DOCUMENTS

CN 105125205 A 12/2015
CN 106539572 A * 3/2017
(Continued)

*Primary Examiner* — Joseph M Dietrich
*Assistant Examiner* — Michael T. Holtzclaw
(74) *Attorney, Agent, or Firm* — Kinney & Lange, P.A.

(57) ABSTRACT

Embodiments of the present disclosure provide a blood pressure measuring method, a blood pressure measuring apparatus, an electronic device and a computer readable storage medium. The electronic device includes a processor configured to: acquire an electrocardiosignal and a blood oxygen volume wave signal of a target object within a preset measurement period; and determine beat-wise blood pressure values of the target object within the preset measurement period by means of a first trained blood pressure calculation model based on the acquired electrocardiosignal and blood oxygen volume wave signal.

16 Claims, 6 Drawing Sheets

(51) Int. Cl.
*A61B 5/00* (2006.01)
*A61B 5/318* (2021.01)
*A61B 5/0205* (2006.01)

(52) U.S. Cl.
CPC ............ *A61B 5/318* (2021.01); *A61B 5/7267* (2013.01); *A61B 2560/02* (2013.01)

(56) References Cited

U.S. PATENT DOCUMENTS

| | | |
|---|---|---|
| 2011/0009755 A1 | 1/2011 | Wenzel et al. |
| 2017/0042433 A1* | 2/2017 | Noh ...................... A61B 5/1118 |
| 2018/0085012 A1* | 3/2018 | Wei .................... A61B 5/14542 |

FOREIGN PATENT DOCUMENTS

| | | | | |
|---|---|---|---|---|
| CN | 106539572 A | | 3/2017 | |
| CN | 106889979 A | * | 6/2017 | |
| CN | 106889979 A | | 6/2017 | |
| CN | 109044302 A | | 12/2018 | |
| WO | WO-2019019491 A1 | * | 1/2019 | ............. A61B 5/021 |

* cited by examiner

BLOOD PRESSURE MEASURING APPARATUS, BLOOD PRESSURE MEASURING METHOD, ELECTRONIC DEVICE, AND COMPUTER READABLE STORAGE MEDIUM

CROSS-REFERENCE TO RELATED APPLICATION(S)

This application is the national phase of PCT Application No. PCT/CN2019/074215 filed on Jan. 31, 2019, which in turn claims priority to Chinese Application No. 201810716583.6, entitled "BLOOD PRESSURE MEASURING APPARATUS, ELECTRONIC DEVICE, AND COMPUTER READABLE STORAGE MEDIUM" and filed on Jul. 3, 2018, both of which are incorporated herein by reference in their entireties.

TECHNICAL FIELD

The present disclosure relates to the field of intelligent medical technologies, and in particular, to a blood pressure measuring apparatus, a blood pressure measurement method, an electronic device, and a computer-readable storage medium.

BACKGROUND

A blood pressure refers to a lateral pressure applied on a blood vessel wall per unit area when blood flows in the blood vessel, which is a dynamic force for promoting the blood to flow in the blood vessel. The blood pressure includes a diastolic blood pressure and a systolic blood pressure. The blood pressure is also an important physiological parameter reflecting cardiovascular functions, and an important basis for diagnosing diseases, observing treatment effects and post-treatment judgment. Therefore, how to measure the blood pressure becomes a key problem.

The current pulse wave sphygmomanometer based on the pulse wave principle uses an upper arm cuff with downstream pulse wave detection, in which discontinuous events of pulse beating are converted into a continuous measurement, and subjective judgment on whether there are Korotkoff sounds or not is converted into measuring the amplitude characteristic of the pulse wave near the systolic blood pressure or measuring the time characteristic of the delay time between the pulse wave and the corresponding barometric alternating current signal near the diastolic blood pressure, so that the systolic blood pressure and the diastolic blood pressure are calculated according to the amplitude characteristic near the systolic blood pressure or the time characteristic near the diastolic blood pressure.

SUMMARY

The present disclosure provides a blood pressure measuring method, a blood pressure measuring apparatus, an electronic device and a computer readable storage medium.

In a first aspect, there is provided an electronic device. The electronic device includes:

a processor configured to:

acquire an electrocardiosignal and a blood oxygen volume wave signal of a target object within a preset measurement period; and determine beat-wise blood pressure values of the target object within the preset measurement period by means of a first trained blood pressure calculation model based on the acquired electrocardiosignal and blood oxygen volume wave signal.

According to an embodiment of the present disclosure, the blood pressure values include a diastolic blood pressure and a systolic blood pressure, and the processor is further configured to, after the beat-wise blood pressure values of the target object within the preset measurement period are determined, determine an error value corresponding to a diastolic blood pressure of each beat of the target object within the preset measurement period and an error value corresponding to a systolic blood pressure of each beat of the target object within the preset measurement period by means of a second trained blood pressure calculation model based on the acquired electrocardiosignal and blood oxygen volume wave signal; and correct the diastolic blood pressure of the corresponding beat determined by means of the first trained blood pressure calculation model based on the error value corresponding to the diastolic blood pressure of each beat of the target object within the preset measurement period so as to determine the corrected beat-wise diastolic blood pressures of the target object within the preset measurement period; and correct the systolic blood pressure of the corresponding beat determined by means of the first trained blood pressure calculation model based on the error value corresponding to the systolic blood pressure of each beat of the target object within the preset measurement period so as to determine the corrected beat-wise systolic blood pressures of the target object within the preset measurement period.

According to an embodiment of the present disclosure, the processor is further configured to, before the beat-wise blood pressure values of the target object within the preset measurement period are determined based on the acquired electrocardiosignal and blood oxygen volume wave signal by means of the first trained blood pressure calculation model:

perform a differential processing on the acquired blood oxygen volume wave signal to obtain a plurality of characteristic values of the blood oxygen volume wave signal;

determine a pulse wave transmission time 'PTT' based on a maximum of a first derivative of the blood oxygen volume wave signal in the same cycle where the electrocardiosignal is located and an instant value of an R point of the electrocardiosignal; and perform a principal component analysis processing on the PTT and the plurality of characteristic values of the blood oxygen volume wave signal, and extract principal component factors that satisfy a preset condition to obtain a principal component factor matrix.

According to an embodiment of the present disclosure, the processor is further configured to determine the beat-wise blood pressure values of the target object within the preset measurement period by means of the first trained blood pressure calculation model based on the acquired electrocardiosignal and blood oxygen volume wave signal by:

inputting the principal component factor matrix to the first trained blood pressure calculation model to determine the diastolic blood pressure and the systolic blood pressure of the beat corresponding to the principal component factor matrix;

wherein the processor is further configured to determine the error value corresponding to the diastolic blood pressure of a beat of the target object within the preset measurement period and the error value corresponding to the systolic blood pressure of the beat of the target object within the preset measurement period by means of the second trained blood pressure calculation model based on the acquired electrocardiosignal and blood oxygen volume wave signal by:

inputting the principal component factor matrix to the second trained blood pressure calculation model to determine the error value corresponding to the diastolic blood pressure and the error value corresponding to the systolic blood pressure of the beat corresponding to the principal component factor matrix.

According to an embodiment of the present disclosure, the processor is further configured to, before the beat-wise blood pressure values of the target object within the preset measurement period are determined based on the acquired electrocardiosignal and blood oxygen volume wave signal by means of the first trained blood pressure calculation model:

train an Elman neural network to obtain the first trained blood pressure calculation model.

According to an embodiment of the present disclosure, the processor is further configured to train the Elman neural network to obtain the first trained blood pressure calculation model by:

training the Elman neural network by taking a plurality of principal component factor matrixes acquired within a preset sampling period, and reference values of the diastolic blood pressures and reference values of the systolic blood pressures which are measured at the same beats as those for the respective principal component factor matrixes within the preset sampling period as training samples, so as to obtain the first trained blood pressure calculation model, wherein the principal component factor matrixes are obtained by performing differential processing and principal component analysis based on the electrocardiosignals and blood oxygen volume wave signals.

According to an embodiment of the present disclosure, the processor is further configured to, before the error value corresponding to the diastolic blood pressure of each beat of the target object within the preset measurement period and the error value corresponding to the systolic blood pressure of each beat of the target object within the preset measurement period are determined based on the acquired electrocardiosignal and blood oxygen volume wave signal by means of the second trained blood pressure calculation model:

train a linear neural network to obtain the second trained blood pressure calculation model.

According to an embodiment of the present disclosure, the processor is further configured to train the linear neural network to obtain the second trained blood pressure calculation model by:

training the linear neural network by taking a plurality of principal component factor matrixes acquired within a preset sampling period and blood pressure error information corresponding to the respective principal component factor matrixes as training samples, so as to obtain the second trained blood pressure calculation model;

wherein the blood pressure error information comprises: diastolic blood pressure error information and systolic blood pressure error information, wherein the diastolic blood pressure error information is a difference between the diastolic blood pressure output in the training process of the Elman neural network and the reference value of the diastolic blood pressure measured at the same beat; and the systolic blood pressure error information is a difference between the systolic blood pressure output in the training process of the Elman neural network and the reference value of the systolic blood pressure measured at the same beat.

In a second aspect, there is provided a blood pressure measuring method. The blood pressure measuring method includes: acquiring an electrocardiosignal and a blood oxygen volume wave signal of a target object input within a preset measurement period; and determining beat-wise blood pressure values of the target object within the preset measurement period by means of a first trained blood pressure calculation model based on the acquired electrocardiosignal and blood oxygen volume wave signal.

In a third aspect, there is provided a blood pressure measuring apparatus. The blood pressure measuring apparatus includes:

an acquisition module, configured to acquire an electrocardiosignal and a blood oxygen volume wave signal of a target object input within a preset measurement period; and a determination module, configured to determine beat-wise blood pressure values of the target object within the preset measurement period by means of a first trained blood pressure calculation model based on the electrocardiosignal and blood oxygen volume wave signal acquired by the acquisition module.

In a fourth aspect, there is provided a computer-readable storage medium on which a computer program is stored, the computer program, which when executed by a processor, causes the processor to:

acquire an electrocardiosignal and a blood oxygen volume wave signal of a target object within a preset measurement period; and determine beat-wise blood pressure values of the target object within the preset measurement period by means of a first trained blood pressure calculation model based on the acquired electrocardiosignal and blood oxygen volume wave signal.

BRIEF DESCRIPTION OF THE DRAWINGS

In order to illustrate the technical solutions in the embodiments of the present disclosure more clearly, the drawings that are required to be used in the description of the embodiments of the present disclosure will be briefly described below.

DETAILED DESCRIPTION

Figure 1A:
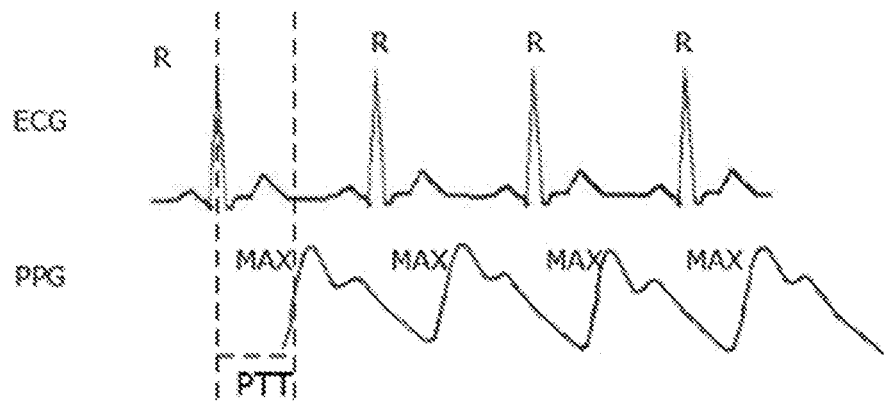
FIG. 1a is a schematic diagram of a pulse wave transmission time measurement by a combination of ECG and PPG.

The embodiments of the present disclosure are described in detail below, and the examples of the embodiments are illustrated in the drawings, wherein the same or similar reference numerals are used to refer to the same or similar elements or elements having the same or similar functions. The embodiments described below with reference to the drawings are illustrative only for explaining the present disclosure, but are not to be construed as limiting the present disclosure.

It is to be understood by the skilled in the art that the singular forms "a", "an", "the" and "said" may include the plural forms, unless otherwise specified. It should be further understood that the phrase "comprise" used in the description of the present disclosure means that there are the features, integers, steps, operations, elements, and/or components, but does not exclude one or more other features, integers, steps, operations, elements, components and/or groups thereof. It should be understood that when it is described that an element is "connected" to another element, it may be connected to the other element directly or via an intermediate element. In addition, "connected" as used herein may include connected in a wireless way. The phrase "and/or" used herein includes all or any one of one or more associated listed items and all combinations thereof.

Currently, the non-invasive blood pressure measuring devices sold in the market are divided into two categories, namely a mercury sphygmomanometer and an electronic sphygmomanometer. Most of the non-invasive blood pressure measuring devices sold in the market adopt a cuff-type measuring mode, and utilize a measuring principle of an oscillography method or a Korotkoff sound method.

The oscillography method is a method of simultaneously recording pulse waves and pressures to detect the blood pressure. The specific methods for determining the systolic blood pressure and the diastolic blood pressure based on the oscillometric principle are mainly classified into two categories. One category is called a waveform feature method, in which the blood pressure is distinguished by identifying waveform features of pressure waves at the systolic blood pressure and the diastolic blood pressure. However, when the blood pressure is measured by the waveform feature method, the accuracy of the blood pressure measured by the waveform feature method is lower because the waveform features cannot be extracted accurately and effectively, and the extracted waveform features cannot be adapted to individual difference, etc. Another category is called an amplitude coefficient method, in which the blood pressure is distinguished by determining a relationship between a systolic blood pressure amplitude, a diastolic blood pressure amplitude and the maximum amplitude. However, the amplitude coefficient used when the blood pressure is measured by the amplitude coefficient method is an empirical value obtained statistically, and is not set for some individual, resulting in inaccurate measurement results.

The Korotkoff sound method, which is the most common blood pressure measurement method in clinic, is easy to cause a false judgment, such as a false higher pressure or a false lower pressure, due to the defects in the theory of its own, and thus its measurement is not accurate.

In addition, the pulse wave sphygmomanometer based on the pulse wave principle uses the upper arm cuff with the downstream pulse wave detection, in which discontinuous events of pulse beating are converted into a continuous measurement, and subjective judgment on whether there are Korotkoff sounds or not is converted into measuring the amplitude characteristic of the pulse wave near the systolic blood pressure or measuring the time characteristic of the delay time between the pulse wave and the corresponding barometric alternating current signal near the diastolic blood pressure; and the systolic blood pressure and the diastolic blood pressure are calculated according to the amplitude characteristic near the systolic blood pressure or the time characteristic near the diastolic blood pressure, so as to avoid the error caused by the subjective judgment on whether there are Korotkoff sounds or not. However, the blood pressure measurement based on the pulse wave principle can only obtain one diastolic blood pressure and one corresponding systolic blood pressure in the measuring process, which belongs to discontinuous blood pressure measurement.

The blood pressure is an important physiological parameter reflecting cardiovascular functions, and is an important basis for diagnosing diseases, observing treatment effects and post-treatment judgment. Since the blood pressure is affected by factors, such as physical conditions, emotional environmental conditions, and physiological rhythm, the blood pressure value may change over time, and the blood pressure value measured at a single time cannot indicate the actual condition of the blood pressure of the tested person. Compared with a single blood pressure value, continuous blood pressure values can reflect the actual condition of the blood pressure better.

How to ensure that the continuous blood pressure values can be conveniently, accurately and reliably measured under the non-invasive condition is a critical technology to be solved. Currently, continuous blood pressure is measured mainly by such methods as arterial tension, volume compensation, pulse wave transmission time, and the like.

The principle of the arterial tension method is that when a blood vessel with an internal pressure is flattened by an external force, an internal stress of the vessel wall changes; when the external force reaches a certain value, the internal pressure of the blood vessel is equal to the external force; and at this time, an arterial blood pressure may be obtained by measuring the external force, and meanwhile, a central arterial pressure is calculated according to a correlation between the peripheral arterial blood pressure and the central arterial pressure. However, when the blood pressure is measured by this method, it is difficult to maintain a measurement position of a sensor relatively fixed for a long time due to a high sensitivity of the sensor to displacement, and an air bag pressurizing apparatus also affects the comfort of the tested person during a long-time measurement. Therefore, the arterial tension method is not suitable for the long-time measurement of the blood pressure.

The principle of the volume compensation method is that when the arterial blood vessel is in an offload state under the effect of the external force, the external pressure is equal to the arterial pressure, the diameter of the blood vessel cannot change with the fluctuation of the blood pressure, and the blood vessel is in a constant volume state. By presetting a reference pressure to make the artery in the offload state, and also adjusting the external pressure by a quick-response pressure control system according to the blood pressure fluctuation time so that the artery is always in the constant volume state, the dynamic arterial blood pressure value may be obtained by measuring the external pressure. The volume compensation method may be used to continuously measure the blood pressure waveform per pulse. However, due to the application of the air bag pressure, measurement for a long time may cause venous congestion and thus may influence the measurement precision; and also, the tested person may feel discomfort.

Figure 1B:
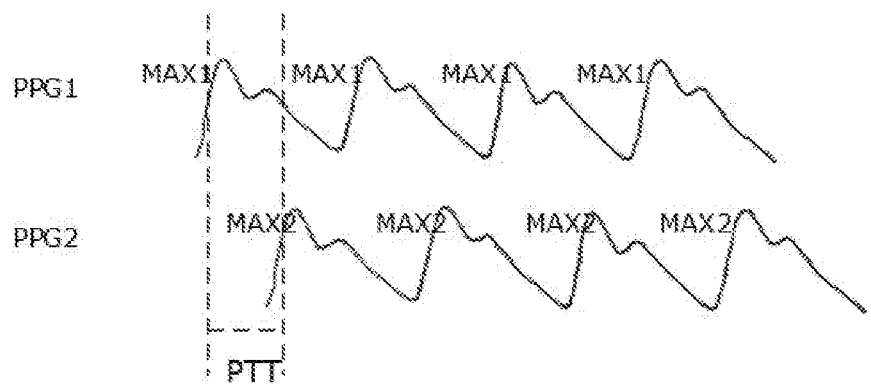
FIG. 1b is a schematic diagram of a pulse wave transmission time measurement by means of dual PPG.

Currently, the methods of measuring the continuous blood pressure non-invasively by using the pulse wave transmission time approach are hot in research. The methods of measuring the continuous blood pressure non-invasively by using the pulse wave transmission time approach may be classified into two types: (1) an approach of combining an Electrocardiogram (ECG) signal and a Photo Plethysmograph (PPG) waveform, as shown in FIG. 1a, that is, calculating a time difference PTT between an R point of the electrocardiosignal and a PPG characteristic point by collecting the ECG of a first lead and collecting the PPG of a finger or a wrist or a back of hand in a transmission or reflection way simultaneously, and then reversely deriving the continuous blood pressure by utilizing the relationship between the pulse wave transmission time and the systolic blood pressure or average pressure; and (2) an dual-PPG approach, as shown in FIG. 1b, that is, placing one reflective photoelectric sensor on each of the wrist and the back of hand, or placing one reflective photoelectric sensor at each of two different positions of a finger, calculating a time difference PTT between the corresponding characteristic points respectively on the two PPGs, and then reversely deriving the continuous blood pressure by utilizing the relationship between the pulse wave transmission time and the systolic blood pressure or average pressure. However, the accuracy of measuring the continuous blood pressure non-invasively by these two approaches is still not high.

In view of the above problems, the embodiments of the present disclosure provide an electronic device for measuring blood pressure. According to the blood pressure formation mechanism and the hemodynamic principle, it may be known that the cardiac output, circulating blood volume, blood vessel wall elasticity and peripheral resistance are main factors influencing the blood pressure variation, the artificial factors such as respiration and emotion are also closely related to the blood pressure variation; and meanwhile, the blood pressure is also influenced by age and physical conditions.

Generally, when the cardiac output increases, the blood pressure increases, causing that the difference between the first peak amplitude and the minimum amplitude of the pulse wave becomes smaller, the pulse wave transmission time becomes longer, and the systolic area increases; when the peripheral resistance is reduced, the blood pressure increases, causing that the amplitude of the first peak point of the pulse wave increases, the amplitude of the tangential point of the pulse wave decreases, and the difference between the first peak and the second peak of the pulse wave reduces, wherein the variations of the diastolic area and the ratio of the systolic area and the diastolic area represent increase or decrease of the total vascular resistance; when the elasticity of the blood vessel wall becomes weaken, the blood pressure increases, causing that the pulse wave transmission time reduces, the amplitude of the second peak point of the pulse wave decreases, the time difference between the tangential points of the two adjacent pulse waves increases, the difference between the first peak amplitude and the second peak amplitude increases, and the growth coefficient is changed.

The circulating blood volume is relatively constant for an individual, but when the circulating blood volume reduces, the blood pressure reduces, directly causing that the minimum amplitude of the pulse wave and the first peak amplitude of the pulse wave reduce, and the area of the blood oxygen volume wave reduces; and when the respiration is accelerated, the blood pressure increases, causing that the first peak amplitude of the pulse wave, the time difference between the first peaks of two adjacent pulse waves, and the minimum point of the adjacent pulse waves also change with the variation of the respiration. The blood pressure is also regulated by the nervous system, and the variation of the nervous system may be shown by means of the heart rate variability of the electrocardiosignal, and may also be shown by means of the pulse rate variability and the second peak variability of the pulse wave. That is, the variation of the nervous system may cause variations of the time difference between the second peaks of two adjacent pulse waves and of the time difference between the first peaks of two adjacent pulse waves. The difference between the second peak variability of the pulse wave and the pulse rate variability is that the second peak of the pulse wave is a signal reflected back after being transmitted to the lower half of the body, so that the second peak variability of the pulse wave includes information of other parameters, such as the blood vessel wall elasticity, the blood vessel resistance, etc., of the circulatory system on the reflection path, in addition to the common parameters, such as the blood density, the blood flow velocity, etc., that are reflected by the first peak of the pulse wave. Meanwhile, the waveform of the blood oxygen volume wave may be varied with the factors such as the increase of age, the change of physical health conditions and the like, which directly causes variations of three parameters, i.e., the rising time from the minimum point to the first peak point in the same cycle, the time increment from the first peak point to the second peak point in the same cycle, and the time increment from the tangential point to the minimum point in the same cycle.

In summary, the parameters related to the blood pressure include: the pulse wave transmission time, the time difference between two first peak points of the blood oxygen volume wave in two adjacent cycles, the time difference between two minimum points, the time difference between two second peak points, the time difference between two adjacent tangential points, the amplitude of the first peak point of the blood oxygen volume wave in a cycle, the minimum amplitude, the amplitude of the second peak point, the amplitude of the tangential point, the systolic area, the diastolic area, the area and the area ratio of the blood oxygen volume wave, the difference between the first peak point amplitude and the second peak point amplitude of the blood oxygen volume wave in the same cycle, the difference between the first peak point amplitude and the minimum point amplitude of the blood oxygen volume wave in the same cycle, the rising time from the minimum point to the first peak point in the same cycle, the time increment from the first peak point to the second peak point in the same cycle, the time increment from the tangential point to the minimum point in the same cycle, and the growth coefficient.

Therefore, the embodiments of the present disclosure calculate these parameter values, and then determine the beat-wise diastolic blood pressure and systolic blood pressure based on the calculated parameter values.

The technical solutions of the present disclosure and how the technical solutions of the present disclosure solve the above technical problems will be described in detail with specific examples below. The following specific embodiments may be combined with each other, and the same or similar concepts or processes may not be described in detail in some embodiments. The embodiments of the present disclosure will be described below with reference to the accompanying drawings.

Figure 1C:
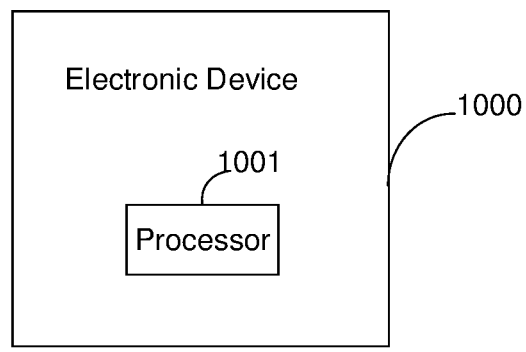
FIG. 1c is a schematic structural diagram of an electronic device for measuring a blood pressure according to an embodiment of the present disclosure.
Figure 1D:
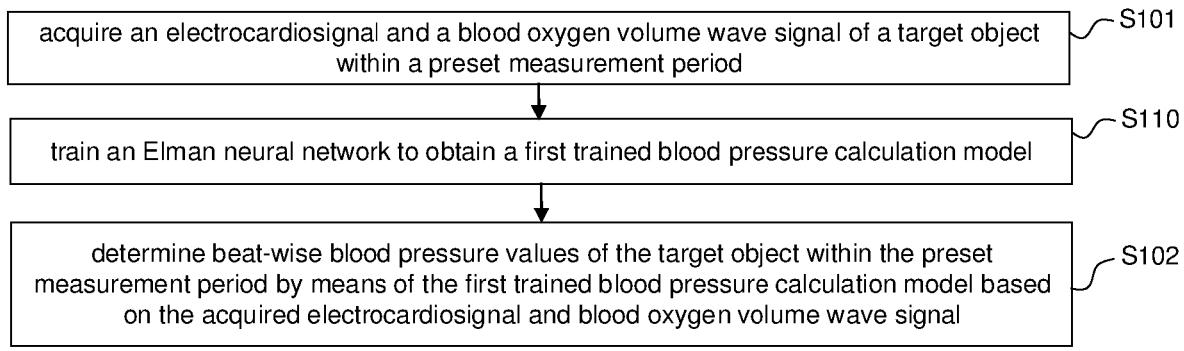
FIG. 1d is a flowchart of measuring a blood pressure by an electronic device according to an embodiment of the present disclosure.

An embodiment of the present disclosure provides an electronic device, as shown in FIG. 1c. The electronic device 1000 shown in FIG. 1c includes: a processor 1001, wherein the processor 1001 is configured to perform the operations as shown in FIG. 1d.

In step S101, an electrocardiosignal and a blood oxygen volume wave signal of a target object within a preset measurement period are acquired.

According to an embodiment of the present disclosure, the electrocardiosignal is a bioelectric signal generated by the excitation of the cardiac muscle during the heart activity. In an embodiment of the present disclosure, the electrocardiographic signal may be recorded by an electrocardiograph machine.

For an embodiment of the present disclosure, the blood oxygen volume wave is used to represent the variation of blood oxygen concentration in blood per unit volume. According to an embodiment of the present disclosure, the blood oxygen volume wave signal of the target object may be continuously detected by the existing blood oxygen volume wave measuring method. The blood oxygen volume wave signal of the target subject is continuously detected, for example, by a photoplethysmography method.

According to an embodiment of the present disclosure, the preset measurement period may be set by the electronic device or the user, which is not limited in the embodiments of the present disclosure. For example, the preset measurement period may be 1 minute, 2 minutes, or the like.

According to an embodiment of the present disclosure, the way of acquiring the electrocardiosignal and the blood oxygen volume wave signal of the target object within the preset measurement period may comprise acquiring the electrocardiosignal and the blood oxygen volume wave signal of the target object within the preset measurement period in real time, or receiving the input electrocardiosignal and the blood oxygen volume wave signal of the target object measured within the preset measurement period, which is not limited by the embodiments of the present disclosure. In an embodiment of the present disclosure, the measurement periods of the electrocardiosignal and the blood oxygen volume wave signal are the same.

According to an embodiment of the present disclosure, the target object is a user who needs to measure the beat-wise blood pressure.

In step S102, beat-wise blood pressure values of the target object within the preset measurement period are determined based on the acquired electrocardiosignal and blood oxygen volume wave signal by means of a first trained blood pressure calculation model.

The blood pressure values may include a diastolic blood pressure and a systolic blood pressure.

According to an embodiment of the present disclosure, the determination of the beat-wise blood pressure values of the target object within the preset measurement period means that one diastolic blood pressure and one corresponding systolic blood pressure may be determined upon one beat of the heart or pulse within the preset measurement period.

For example, if the preset measurement period is 1 minute, and the target object' heart beats 60 times within 1 minute, 60 diastolic blood pressures and corresponding 60 systolic blood pressures of the target object are determined within 1 minute.

An embodiment of the present disclosure provides an electronic device. The electronic device includes a processor configured to: acquire an electrocardiosignal and a blood oxygen volume wave signal of a target object within a preset measurement period; and then determine beat-wise blood pressure values of the target object within the preset measurement period by means of a first trained blood pressure calculation model based on the acquired electrocardiosignal and blood oxygen volume wave signal. That is, the electronic device may acquire a plurality of continuous diastolic blood pressures and a plurality of corresponding continuous systolic blood pressures within the preset measurement period based on the electrocardiosignal and the blood oxygen volume wave signal measured within the preset measurement period. For example, 60 diastolic blood pressures and the corresponding 60 systolic blood pressures, instead of only one diastolic blood pressure and one systolic blood pressure, are acquired within a measurement period of 1 minute, so that the accuracy of measuring the blood pressure may be improved.

Figure 2A:
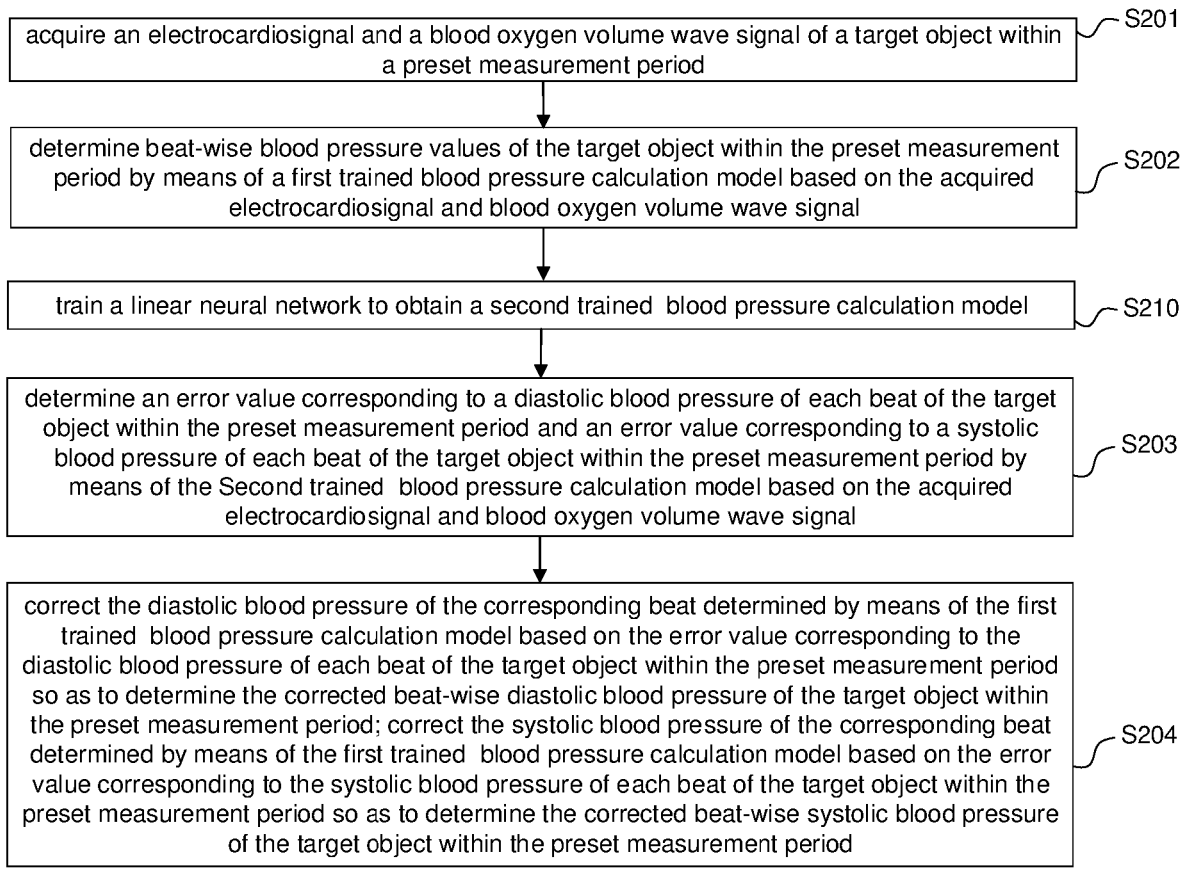
FIG. 2a is another flowchart of measuring a blood pressure by an electronic device according to an embodiment of the present disclosure.

In another possible implementation manner of an embodiment of the present disclosure, the processor 1001 is further configured to perform steps as shown in FIG. 2a on the basis of implementing the steps as shown in FIG. 1d, in which step S102 is followed by step S203 and step S204, wherein the operations performed in step S201 and step S202 are the same as those performed in step S101 and step S102, and are thus not repeated herein.

In step S203, an error value corresponding to a diastolic blood pressure of each beat of the target object within the preset measurement period and an error value corresponding to a systolic blood pressure of each beat of the target object within the preset measurement period are determined based on the acquired electrocardiosignal and blood oxygen volume wave signal by means of a second trained blood pressure calculation model.

According to an embodiment of the present disclosure, since the beat-wise diastolic blood pressure and the corresponding beat-wise systolic blood pressure obtained by means of the first trained blood pressure calculation model may have errors compared with the true diastolic blood pressure and systolic blood pressure of the target object, in order to improve the accuracy of the output beat-wise diastolic blood pressure and corresponding beat-wise systolic blood pressure, the beat-wise diastolic blood pressure and the corresponding beat-wise systolic blood pressure output by means of the first trained blood pressure calculation model are corrected by the beat-wise diastolic blood pressure error and the corresponding beat-wise systolic blood pressure error output by means of the second blood pressure calculation model.

In step S204, based on the error value corresponding to the diastolic blood pressure of each beat of the target object within the preset measurement period, the diastolic blood pressure of the corresponding beat determined by means of the first trained blood pressure calculation model is corrected so as to determine the corrected beat-wise diastolic blood pressures of the target object within the preset measurement period; and based on the error value corresponding to the systolic blood pressure of each beat of the target object within the preset measurement period, the systolic blood pressure of the corresponding beat determined by means of the first trained blood pressure calculation model is corrected so as to determine the corrected beat-wise systolic blood pressures of the target object within the preset measurement period.

For an embodiment of the present disclosure, if the diastolic blood pressure of a beat that is output by means of the first trained blood pressure calculation model is denoted by $BP_1$, the corresponding systolic blood pressure is denoted by $BP_2$, the error value corresponding to the diastolic blood pressure of the beat that is output by means of the second trained blood pressure calculation model is denoted by $BP\_error_1$, and the error value corresponding to the corresponding systolic blood pressure is denoted by $BP\_error_2$, the corrected diastolic blood pressure of the beat of the target object is $Output\_BP_1 = BP\_error_1 + BP_1$, and the corrected systolic blood pressure of the beat of the target object is $Output\_BP_2 = BP\_error_2 + BP_2$.

According to the embodiments of the present disclosure, the error value corresponding to the diastolic blood pressure of each beat of the target object within the preset measurement period and the error value corresponding to the systolic blood pressure of each beat of the target object within the preset measurement period are obtained by inputting the electrocardiosignal and the blood oxygen volume wave signal to the second trained blood pressure calculation model, and the diastolic blood pressure and the systolic blood pressure obtained by means of the first trained blood pressure calculation model are respectively corrected by the obtained error values to obtain the corrected beat-wise diastolic blood pressures and beat-wise systolic blood pressures. Therefore, the accuracy of the determined blood pressure value may be further improved, improving the user experience.

Figure 2B:
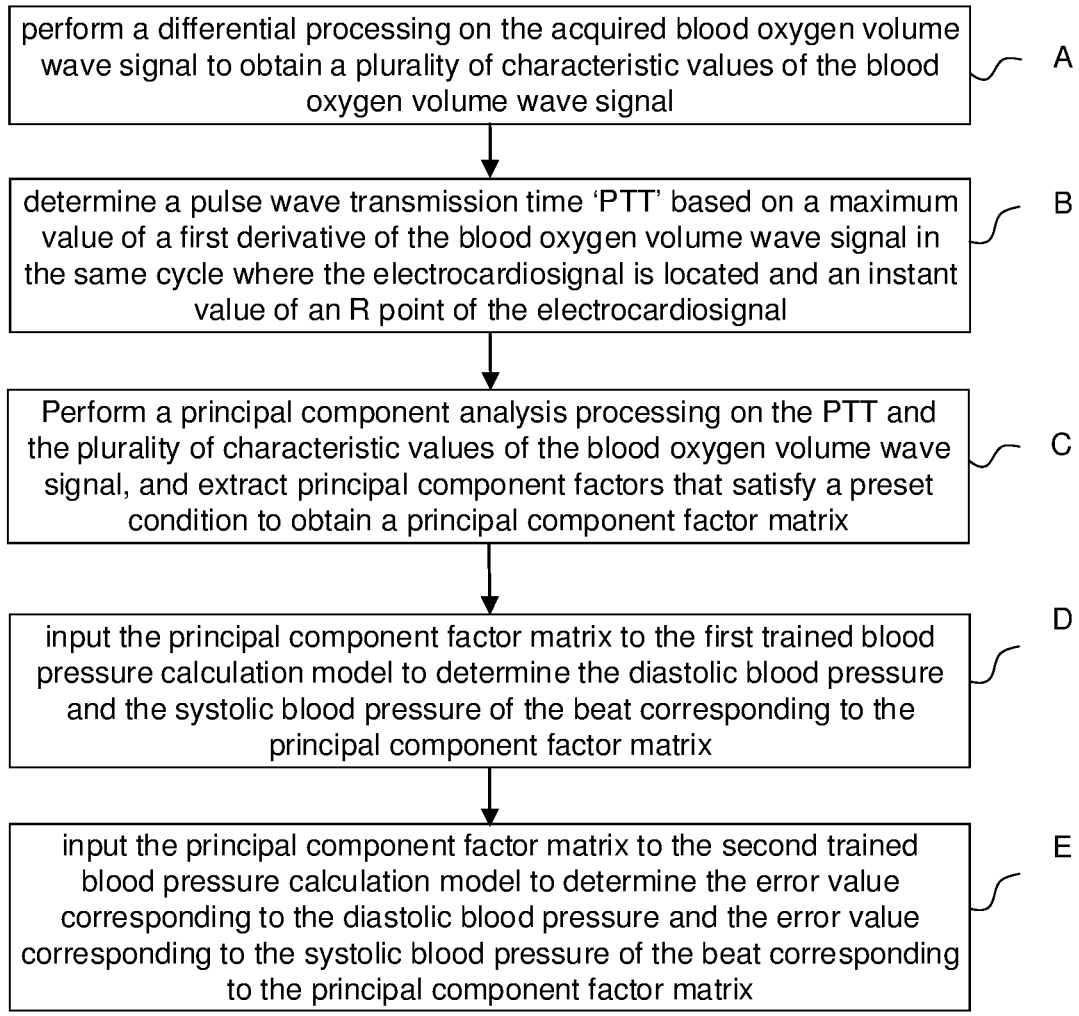
FIG. 2b is yet another flowchart of measuring a blood pressure by an electronic device according to an embodiment of the present disclosure.

In another possible implementation of an embodiment of the present disclosure, the processor 1001 is configured to perform steps A, B and C as shown in FIG. 2b before the beat-wise blood pressure values of the target object within the preset measurement period are determined based on the acquired electrocardiosignal and blood oxygen volume wave signal by means of the first trained blood pressure calculation model.

In step A, a differential processing is performed on the acquired blood oxygen volume wave signal to obtain a plurality of characteristic values of the blood oxygen volume wave signal.

Figure 2C:
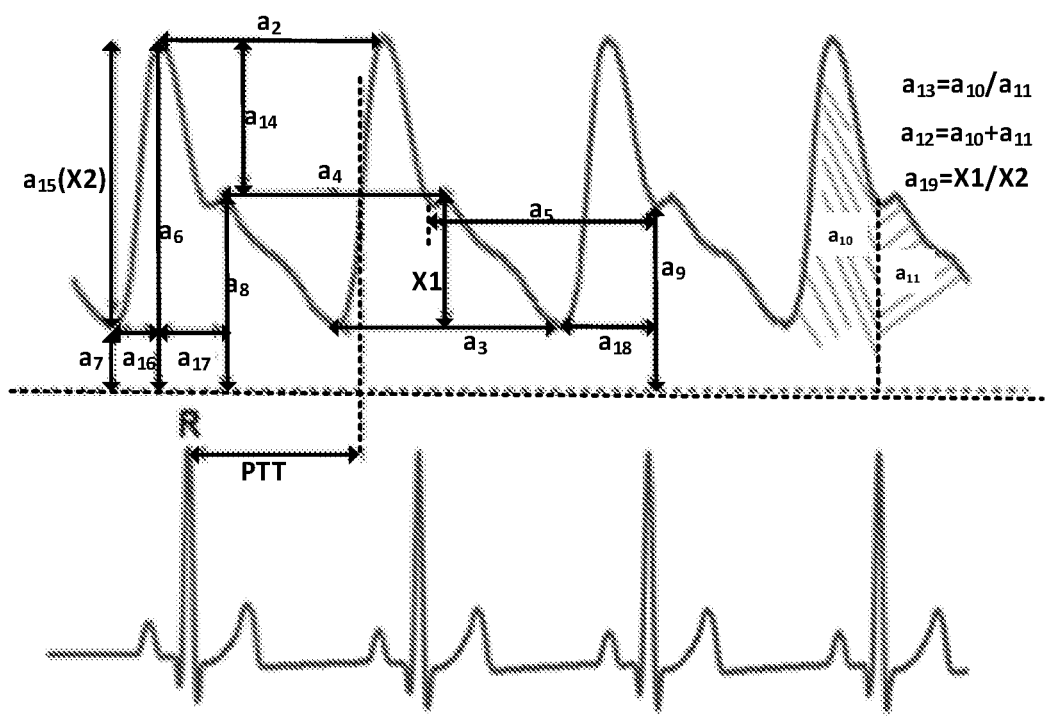
FIG. 2c is a schematic diagram of characteristic values of an electrocardiosignal and a blood oxygen volume wave signal.

According to an embodiment of the present disclosure, the plurality of characteristic values of the blood oxygen volume wave signal that are obtained by performing the differential processing on the acquired blood oxygen volume wave signal include: a time difference $a_2$ between two first peak points of the blood oxygen volume wave in two adjacent cycles, a time difference $a_3$ between two minimum points, a difference $a_4$ between two second peak points, a difference as between two tangential points, an amplitude $a_6$ of the first peak point of the blood oxygen volume wave in a cycle, an amplitude $a_7$ of the minimum point, an amplitude $a_8$ of the second peak point, an amplitude $a_9$ of the tangential point, a systolic area $a_{10}$, a diastolic area $a_{11}$, an area $a_{12}$ of the blood oxygen volume wave, an area ratio $a_{13}$, a difference $a_{14}$ between the first peak point amplitude $a_6$ and the second peak point amplitude $a_8$ of the blood oxygen volume wave in the same cycle, a difference $a_{15}$ between the first peak point amplitude $a_6$ and the minimum point amplitude $a_7$ in the same cycle, a rising time $a_{16}$ from the minimum point to the first peak point in the same cycle, a time increment $a_{17}$ from the first peak point to the second peak point in the same cycle, a time increment $a_{18}$ from the tangential point to the minimum point in the same cycle, and a growth coefficient $a_{19}$, as shown in FIG. 2c.

The growth coefficient $a_{19} = X1/X2$, where X1 is an amplitude difference between the second peak point and the minimum point in the same cycle, and X2 is an amplitude difference between the first peak point and the minimum point in this cycle.

In step B, a pulse wave transmission time 'PTT' is determined based on a maximum of a first derivative of the blood oxygen volume wave signal in the same cycle where the electrocardiosignal is located and an instant value of an R point of the electrocardiosignal, wherein the R point of the electrocardiosignal signal is shown in FIG. 2c.

According to an embodiment of the present disclosure, the instant value of the R point of the electrocardiosignal of the target object is detected in real time by a Pan-Tompkins algorithm, which is denoted as $a_{00}$; and the differential processing is performed on the acquired blood oxygen volume wave signal to obtain the maximum $a_{01}$ of the first derivative of the blood oxygen volume wave in the same cycle where the electrocardiosignal is located. In an embodiment of the present disclosure, the pulse wave transmission time is $PTT = |a_{01} - a_{00}|$, as shown in FIG. 2c.

In step C, a principal component analysis processing is performed on the PTT and the plurality of characteristic values of the blood oxygen volume wave signal, and principal component factors that satisfy a preset condition are extracted to obtain a principal component factor matrix.

For an embodiment of the present disclosure, the principal component analysis (PCA) is a statistical method, in which original variables are recombined into a set of new mutually independent integrated variables, and a few of the integrated variables may be taken out as actually required to reflect information of the original variables as much as possible, which is a method for reducing dimensions mathematically.

For an embodiment of the present disclosure, the principal component analysis is performed on 19 characteristic values of PTT, $a_2, a_3, a_4, a_5, a_6, a_7, a_8, a_9, a_{10}, a_{11}, a_{12}, a_{13}, a_{14}, a_{15}, a_{16}, a_{17}, a_{18}$ and $a_{19}$, the principal component factors with the characteristic values larger than 1 are extracted, and the principal component factors with the characteristic values larger than 1 are denoted as $Factor_1, Factor_2, \ldots, Factor_n$, where $n < 19$, and a relational expression between the extracted principal component factors and the original characteristic values is as follows:

$$\begin{bmatrix} Factor_1 \\ Factor_2 \\ \vdots \\ Factor_n \end{bmatrix} = \begin{bmatrix} w1_1 & w1_2 & \ldots & w1_{19} \\ w2_1 & w2_2 & \ldots & w2_{19} \\ \vdots & \vdots & \ddots & \vdots \\ wn_1 & wn_2 & \ldots & wn_{19} \end{bmatrix} \cdot \begin{bmatrix} PTT \\ a_2 \\ \ldots \\ a_{19} \end{bmatrix} = w_{n \times 19} \cdot \begin{bmatrix} PTT \\ a_2 \\ \ldots \\ a_{19} \end{bmatrix},$$

where $W_{n \times 19}$ indicates the principal component analysis as performed.

According to the embodiments of the present disclosure, the differential processing is performed on the blood oxygen volume wave signal to obtain a plurality of characteristic values; the pulse wave transmission time 'PTT' is determined based on the maximum of the first derivative of the blood oxygen volume wave signal in the same cycle where the electrocardiosignal is located and the instant value of the R point of the electrocardiosignal; and the principal component analysis is performed on the PTT and the characteristic values to implement the dimension reduction processing on the data to be input into the first trained blood pressure calculation model and the second trained blood pressure calculation model, so that the time required for calculating the blood pressure value and the blood pressure error value may be reduced.

In another possible implementation of an embodiment of the present disclosure, the processor 1001 is configured to perform step D as shown in FIG. 2b in the process of determining the beat-wise blood pressure values of the target object within the preset measurement period based on the acquired electrocardiosignal and blood oxygen volume wave signal by means of the first trained blood pressure calculation model.

In step D, the principal component factor matrix is input to the first trained blood pressure calculation model to determine the diastolic blood pressure and the systolic blood pressure of the beat corresponding to the principal component factor matrix.

Specifically, the principal component factor matrix, as an input matrix $Input_{1\times n}=\{Factor_1, Factor_2, \ldots, Factor_n\}$, is input to the first trained blood pressure calculation model to obtain an output matrix $Ouput_{1\times 2}=Input_{1\times n}\times A_{m\times N}\times B_{N\times 2}=\{BP_1, BP_2\}$, wherein $\{BP_1, BP_2\}$ are a diastolic blood pressure and a systolic blood pressure corresponding to the principal component factor matrix which is used as the input matrix. The process of training the first blood pressure calculation model and the way of obtaining $A_{m\times N}$ and $B_{N\times 2}$ are described in detail later, and thus are not repeated herein.

Further, the processor 1001 is configured to perform step E as shown in FIG. 2b in the process of determining the error value corresponding to the diastolic blood pressure of a beat of the target object within the preset measurement period and the error value corresponding to the systolic blood pressure of the beat of the target object within the preset measurement period by means of the second trained blood pressure calculation model based on the acquired electrocardiosignal and blood oxygen volume wave signal.

In step E, the principal component factor matrix is input to the second trained blood pressure calculation model to determine the error value corresponding to the diastolic blood pressure and the error value corresponding to the systolic blood pressure of the beat corresponding to the principal component factor matrix.

It should be noted that the steps in FIG. 2b do not necessarily have to be performed in the order as shown. For example, step E may be performed prior to step D, and steps D and E may be performed between or prior to or in parallel with steps A, B and C.

Specifically, the principal component factor matrix, as an input matrix $Input_{1\times n}=\{Factor_1, Factor_2, \ldots, Factor_n\}$, is input to the second trained blood pressure calculation model to obtain an output matrix $Ouput\_error_{1\times 2}=Input_{1\times n}\times C_{n\times 2}=\{BP\_error_1, BP\_error_2\}$, wherein $\{BP\_error1, BP\_error2\}$ are a diastolic blood pressure error value and a systolic blood pressure error value corresponding to the principal component factor matrix which is used as the input matrix. The process of training the second blood pressure calculation model and the way of determining $C_{n\times 2}$ are described later, and thus are not repeated herein.

According to the embodiments of the present disclosure, the data input to the first blood pressure calculation model and the second blood pressure calculation model are the principal component factor matrix, i.e., the input data of the blood pressure calculation model is the data subjected to the dimension reduction processing, so that the time required for calculating the blood pressure value and the blood pressure error value is reduced, and the time required for obtaining the continuous blood pressure is reduced, thus the user experience is improved.

In another possible implementation of an embodiment of the present disclosure, the processor 1001 is further configured to perform step S110 as shown in FIG. 1d before step S102, in which an Elman neural network is trained to obtain the first trained blood pressure calculation model. Although step S110 in FIG. 1d is shown following step S101, the present disclosure is not limited thereto. Step S110 may be performed before step S101, or in parallel with step S101.

For an embodiment of the present disclosure, when the first blood pressure calculation model is trained, the training may be performed through various neural networks. In an embodiment of the present disclosure, the first blood pressure calculation model being obtained by training the Elman neural network is described in detail.

According to an embodiment of the disclosure, the Elman neural network has a strong calculation capability, whose outstanding advantages are strong functions of optimizing calculation and associative memory. Therefore, the first trained blood pressure calculation model obtained by training the Elman neural network has a strong calculation capability and a strong optimization capability, and may promote the capability of processing dynamic information of the first blood pressure calculation model.

Specifically, the processor 1001 is configured to implement the following steps in the process of training the Elman neural network to obtain the first trained blood pressure calculation model: training the Elman neural network by taking a plurality of principal component factor matrixes acquired within a preset sampling period, and reference values of the diastolic blood pressures and reference values of the systolic blood pressures which are measured at the same beats as those for the respective principal component factor matrixes within the preset sampling period as training samples, so as to obtain the first trained blood pressure calculation model.

The principal component factor matrixes are obtained by performing differential processing and principal component analysis on the electrocardiosignals and blood oxygen volume wave signals.

For an embodiment of the present disclosure, $Factor_1$, $Factor_2$, ..., $Factor_n$ obtained within a preset sampling period, and reference values of the diastolic blood pressures and reference values of the systolic blood pressures which are measured at the same time as those for the heartbeat signal and the blood oxygen volume wave signal are continuously input to the Elman neural network so as to train the Elman neural network.

According to an embodiment of the present disclosure, the Elman neural network is a typical local recurrent (global feed forward local recurrent) network, and may be regarded as a recursive neural network with local memory units and local feedback connections. In an embodiment of the present disclosure, the Elman neural network includes: an input layer, an output layer and a middle hidden layer, wherein the input layer is a single layer and is assumed to be n neurons, the n neurons respectively corresponding to the n principal component factors as described above; the output layer is assumed to be two neurons which respectively correspond to the diastolic blood pressure and the systolic blood pressure; and the middle hidden layer is a single layer and is assumed to be N neurons, where $N=[10, 11, 12]$. In an embodiment of the present disclosure, the neurons of the middle hidden layer respectively receive n principal component factors of the neurons of the input layer and the diastolic blood pressure and the systolic blood pressure of the neurons of the output layer in a full-connection mode, and the middle hidden layer is trained by using the n principal component factors and the diastolic blood pressure and the systolic blood pressure to obtain two coefficient matrixes, i.e., $A_{n \times N}$ and $B_{N \times 2}$, so as to realize the training of the Elman neural network, wherein the coefficient matrix $A_{n \times N}$ is associated with the input layer and the middle hidden layer, and the coefficient matrix $B_{N \times 2}$ is associated with the middle hidden layer and the output layer.

According to an embodiment of the present disclosure, the preset sampling period is not less than 5 minutes (min). In the present embodiment, the diastolic blood pressure and the systolic blood pressure of the target object that are continuously measured by the conventional continuous sphygmomanometer may be respectively used as the reference values of the diastolic blood pressure and the systolic blood pressure.

According to the embodiments of the present disclosure, the first trained blood pressure calculation model is trained by taking the plurality of principal component factor matrixes acquired within the preset sampling period, and the reference values of the diastolic blood pressures and the reference values of the systolic blood pressures which are measured at the same beats as those for the respective principal component factor matrixes as training samples, in order to obtain the beat-wise blood pressure values within the preset measurement period.

In another possible implementation of an embodiment of the present disclosure, the processor 1001 is further configured to perform step S210, in which a linear neural network is trained to obtain the second trained blood pressure calculation model, as shown in FIG. 2a before step S203. Although step S210 in FIG. 2a is shown following step S202, the present disclosure is not limited thereto. Step S210 may be performed before step S202, even before step S201, or in parallel with step S201 or step S202.

According to an embodiment of the present disclosure, the linear neural network is the simplest neural network, and may be composed of one or more linear neurons. The linear neural network has high convergence speed and high precision. Thus, the second blood pressure calculation model obtained by training the linear neural network in this step is for the purpose of obtaining the error value of the diastolic blood pressure and the error value of the systolic blood pressure, which improve the precision of the determined error values of the diastolic blood pressure and the systolic blood pressure.

Specifically, the processor 1001 is configured to train the linear neural network to obtain the second trained blood pressure calculation model by training the linear neural network by taking a plurality of principal component factor matrixes acquired within a preset sampling period and blood pressure error information corresponding to the respective principal component factor matrixes as training samples, so as to obtain the second trained blood pressure calculation model.

The blood pressure error information includes: diastolic blood pressure error information and systolic blood pressure error information, wherein the diastolic blood pressure error information is a difference between the diastolic blood pressure output in the training process of the Elman neural network and the reference value of the diastolic blood pressure measured at the same beat; and the systolic blood pressure error information is a difference between the systolic blood pressure output in the training process of the Elman neural network and the reference values of the systolic blood pressure measured at the same beat.

Specifically, the diastolic blood pressure error information is determined by a formula $BPerror_1 = BP_1 - BP_3$, and the systolic blood pressure error information is determined by a formula $BPerror_2 = BP_2 - BP_4$.

$BP_1$ is the diastolic blood pressure output in the training process of the Elman neural network, $BP_2$ is the systolic blood pressure output in the training process of the Elman neural network, $BP_3$ is the reference value of the diastolic blood pressure measured at the same beat with $BP_1$, and $BP_4$ is the reference value of the systolic blood pressure measured at the same beat with $BP_2$. In an embodiment of the present disclosure, both the reference value of the diastolic blood pressure and the reference value of the systolic blood pressure may be continuously measured by using the existing continuous sphygmomanometer.

According to an embodiment of the present disclosure, the plurality of principal component factor matrixes acquired within the preset sampling period, and $BPerror_1$ and $BPerror_2$ corresponding to respective principal component factor matrixes are input to the linear neural network as training samples to train the linear neural network, in order to obtain the second trained blood pressure calculation model.

Specifically, training the linear neural network is actually training a parameter $C_{n \times 2}$ in the linear neural network. $C_{n \times 2}$ is associated with the input layer and the output layer of the linear neural network, wherein the input layer is assumed to be n neurons respectively corresponding to the input n principal component factors, and the output layer is assumed to be 2 layers respectively corresponding to the diastolic blood pressure error information and the systolic blood pressure error information.

According to the embodiments of the present disclosure, the second blood pressure calculation model is trained by taking the respective principal component factor matrixes and the blood pressure error information corresponding to the principal component factor matrixes as training samples to obtain the second trained blood pressure calculation model, so as to correct the blood pressure information output by the first blood pressure calculation model, thereby obtaining more accurate blood pressure information.

Figure 2D:
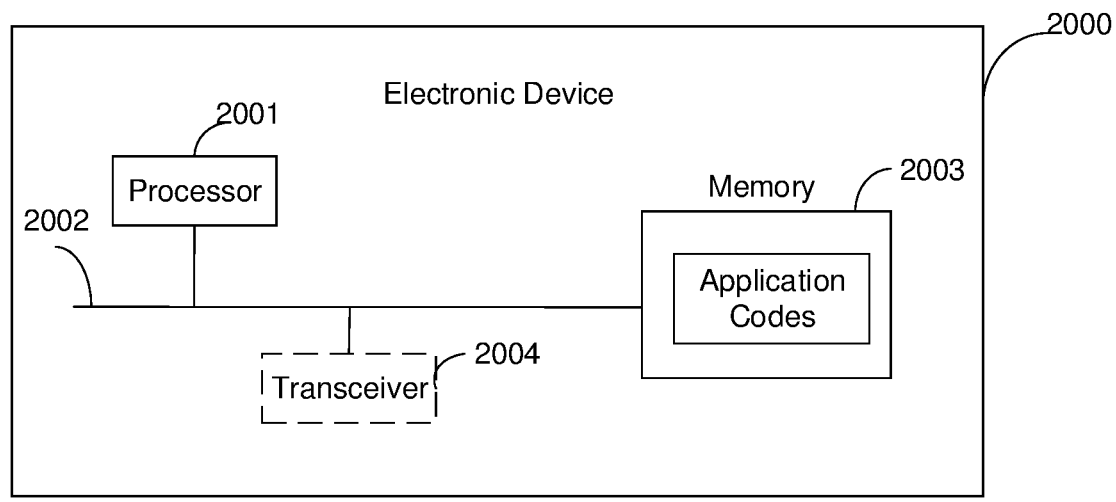
FIG. 2d is another schematic structural diagram of an electronic device for measuring a blood pressure according to an embodiment of the present disclosure.

According to an embodiment of the present disclosure, an electronic device is provided, as shown in FIG. 2d. The electronic device 2000 shown in FIG. 2d includes: a processor 2001 and a memory 2003. The processor 2001 is connected to the memory 2003, such as via a bus 2002. Alternatively, the electronic device 2000 may also include a transceiver 2004. It should be noted that the transceiver 2004 is not limited to one transceiver in practical applications, and the structure of the electronic device 2000 does not make any limitation to the embodiments of the present disclosure.

The transceiver 2004 includes a receiver and a transmitter. The processor 2001 may be a CPU, a general purpose processor, a DSP, an ASIC, an FPGA or other programmable logic devices, a transistor logic device, a hardware component, or any combination thereof, which may implement or execute various exemplary logical blocks, modules, and circuits described in connection with the present disclosure. The processor 2001 may also be a combination of performing computing functions, such as a combination of one or more microprocessors, a combination of a DSP and a microprocessor, and the like.

The bus 2002 may include a path that transfers information between the above components. The bus 2002 may be a PCI bus or an EISA bus, etc. The bus 2002 may be classified into an address bus, a data bus, a control bus, and the like. For ease of illustration, only one bold line is shown for representing the bus in FIG. 2d, but it does not mean that there is only one bus or one type of bus.

The memory 2003 may be ROM or other types of static storage devices that may store static information and instructions, RAM or other types of dynamic storage devices that may store information and instructions, or may be EEPROM, CD-ROM or other optical disk storage, optical disk storage (including compact disks, laser disks, optical disks, digital versatile disks, Blu-ray disks, etc.), a magnetic disk storage medium or other magnetic storage devices, or any other media which can be used to carry or store desired program codes in the form of instructions or data structures and can be accessed by the computer, but are not limited to those.

The memory 2003 is configured to store at least one program which is used for executing the schemes of the present disclosure and is controlled to be executed by the processor 2001. The processor 2001 is configured to execute at least one program stored in the memory 2003 to perform the operations of measuring the blood pressure according to any embodiment of the present application.

The electronic device provided by the embodiments of the present disclosure comprises a processor, which is configured to: acquire the electrocardiosignal and the blood oxygen volume wave signal of the target object within the preset measurement period; and then determine beat-wise blood pressure values of the target object within the preset measurement period by means of the first trained blood pressure calculation model based on the acquired electrocardiosignal and blood oxygen volume wave signal. That is, the electronic device may acquire a plurality of continuous diastolic blood pressures and a plurality of corresponding continuous systolic blood pressures within the preset measurement period based on the electrocardiosignal and the blood oxygen volume wave signal measured within the preset measurement period. For example, 60 diastolic blood pressures and the corresponding 60 systolic blood pressures, instead of only one diastolic blood pressure and one systolic blood pressure, are acquired within a measurement period of 1 minute, so that the accuracy of measuring the blood pressure may be improved.

Figure 3:
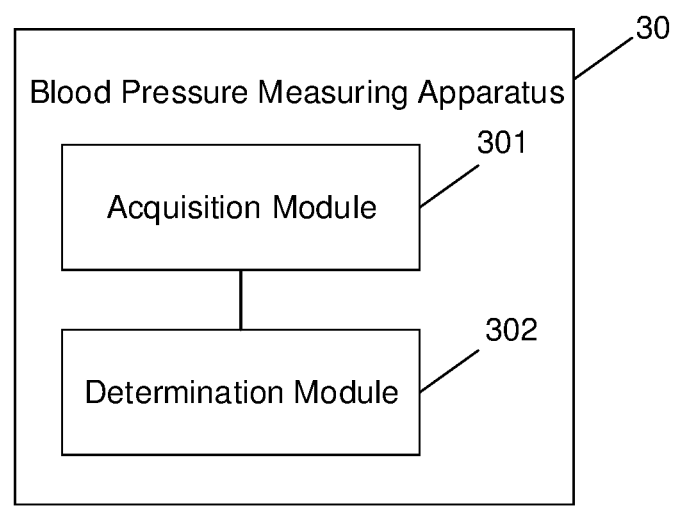
FIG. 3 is a schematic structural diagram of a blood pressure measuring apparatus according to an embodiment of the present disclosure.

An embodiment of the present disclosure provides a blood pressure measuring apparatus as shown in FIG. 3. The blood pressure measuring apparatus 30 may include an acquisition module 301 and a determination module 302.

The acquisition module 301 is configured to acquire an electrocardiosignal and a blood oxygen volume wave signal of a target object within a preset measurement period.

For an embodiment of the present disclosure, the way of acquiring, by the acquisition module 301, the electrocardiosignal and the blood oxygen volume wave signal of the target object within the preset measurement period may comprise acquiring the electrocardiosignal and the blood oxygen volume wave signal of the target object within the preset measurement period in real time, or receiving the input electrocardiosignal and the blood oxygen volume wave signal of the target object measured within the preset measurement period, which is not limited by the embodiments of the present disclosure.

The determination module 302 is configured to determine beat-wise blood pressure values of the target object within the preset measurement period by means of a first trained blood pressure calculation model based on the electrocardiosignal and blood oxygen volume wave signal acquired by the acquisition module 301.

An embodiment of the present disclosure provides a blood pressure measuring apparatus, which includes the acquisition module and the determination module. The acquisition module is configured to acquire the electrocardiosignal and the blood oxygen volume wave signal of the target object within the preset measurement period. The determination module is configured to determine beat-wise blood pressure values of the target object within the preset measurement period by means of the first trained blood pressure calculation model based on the acquired electrocardiosignal and blood oxygen volume wave signal. That is, the blood pressure measuring apparatus may acquire a plurality of continuous diastolic blood pressures and a plurality of corresponding continuous systolic blood pressures within the preset measurement period based on the electrocardiosignal and the blood oxygen volume wave signal measured within the preset measurement period. For example, 60 diastolic blood pressures and the corresponding 60 systolic blood pressures, instead of only one diastolic blood pressure and one systolic blood pressure, are acquired within a measurement period of 1 minute, so that the accuracy of measuring the blood pressure may be improved.

The advantages of the blood pressure measuring apparatus according to an embodiment of the present disclosure are described in detail in the description related to the electronic device described in an embodiment of the present disclosure above, and thus are not repeated herein.

Figure 4:
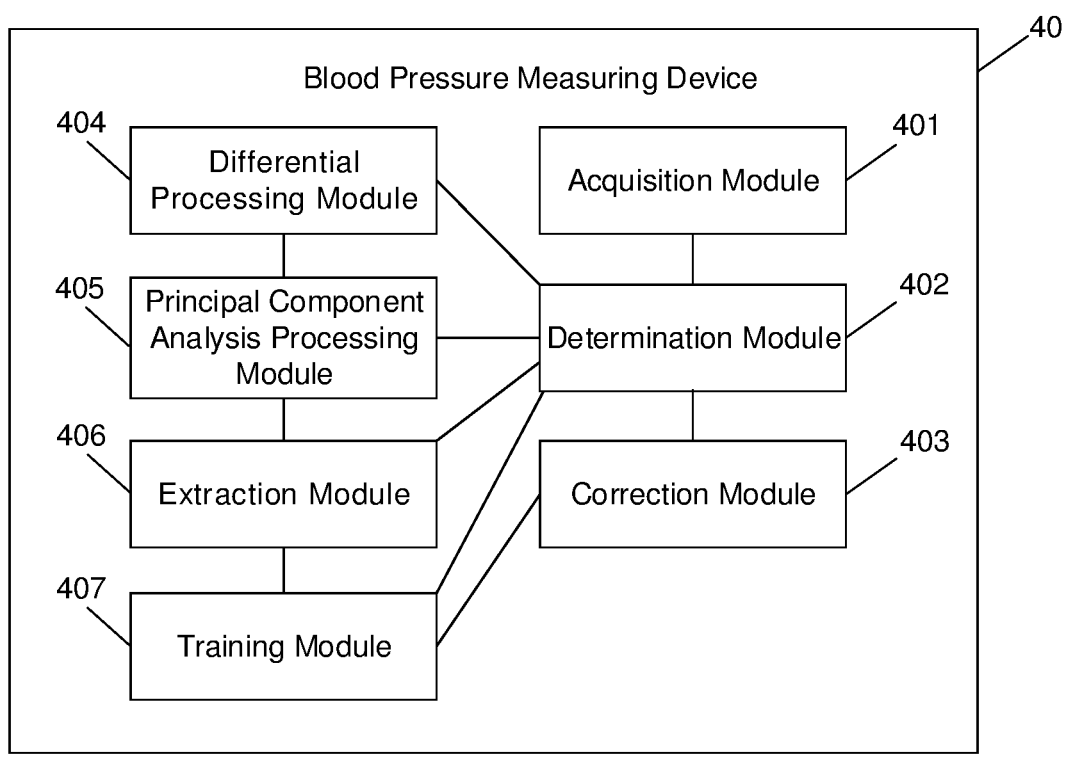
FIG. 4 is another schematic structural diagram of a blood pressure measuring apparatus according to an embodiment of the present disclosure.

Another schematic structural diagram of a blood pressure measuring apparatus provided by an embodiment of the present disclosure is shown in FIG. 4. The blood pressure measuring apparatus 40 may include: an acquisition module 401 and a determination module 402.

The acquisition module 401 is configured to acquire an electrocardiosignal and a blood oxygen volume wave signal of a target object input within a preset measurement period.

The acquisition module 401 in FIG. 4 has the same or similar functions as the acquisition module 301 in FIG. 3.

The determination module 402 is configured to determine beat-wise blood pressure values of the target object within the preset measurement period by means of a first trained blood pressure calculation model based on the electrocardiosignal and blood oxygen volume wave signal acquired by the acquisition module 401.

The acquisition module 402 in FIG. 4 has the same or similar functions as the acquisition module 301 in FIG. 3.

The determination module 402 is further configured to determine an error value corresponding to a diastolic blood pressure of each beat of the target object within the preset measurement period and an error value corresponding to a systolic blood pressure of each beat of the target object within the preset measurement period by means of a second trained blood pressure calculation model based on the electrocardiographic signal and the blood oxygen volume wave signal acquired by the acquisition module 401.

The blood pressure measuring apparatus 40 further includes a correction module 403.

The correction module 403 is configured to correct the diastolic blood pressure of the corresponding beat determined by means of the first trained blood pressure calculation model based on the error value corresponding to the diastolic blood pressure of each beat of the target object within the preset measurement period that is determined by the determination module 402.

The determination module 402 is further configured to determine the corrected beat-wise diastolic blood pressures of the target object within the preset measurement period.

The correction module 403 is further configured to correct the systolic blood pressure of the corresponding beat determined by means of the first trained blood pressure calculation model based on the error value corresponding to the systolic blood pressure of each beat of the target object within the preset measurement period.

The determination module 402 is further configured to determine the corrected beat-wise systolic blood pressures of the target object within the preset measurement period.

For an embodiment of the disclosure, the error value corresponding to the diastolic blood pressure of each beat of the target object within the preset measurement period and the error value corresponding to the systolic blood pressure of each beat of the target object within the preset measurement period are obtained by inputting the electrocardiosignal and the blood oxygen volume wave signal to the second trained blood pressure calculation model, and the diastolic blood pressure and the systolic blood pressure obtained by means of the first trained blood pressure calculation model are respectively corrected by the obtained error values to obtain the corrected beat-wise diastolic blood pressures and beat-wise systolic blood pressures. Therefore, the accuracy of the determined blood pressure value may be further improved, improving the user experience.

The blood pressure measuring apparatus 40 further includes: a differential processing module 404, a principal component analysis processing module 405, and an extraction module 406.

The differential processing module 404 is configured to perform a differential processing on the acquired blood oxygen volume wave signal to obtain a plurality of characteristic values of the blood oxygen volume wave signal.

The determination module 402 is further configured to determine a pulse wave transmission time 'PTT' based on a maximum of a first derivative of the blood oxygen volume wave signal in the same cycle where the electrocardiosignal is located and an instant value of an R point of the electrocardiosignal.

A principal component analysis processing module 405 is configured to perform a principal component analysis processing on the PTT and the plurality of characteristic values of the blood oxygen volume wave signal.

The extraction module 406 is configured to extract principal component factors that satisfy a preset condition to obtain a principal component factor matrix.

For an embodiment of the disclosure, the differential processing is performed on the blood oxygen volume wave signal to obtain a plurality of characteristic values; the pulse wave transmission time 'PTT' is determined based on the maximum of the first derivative of the blood oxygen volume wave signal in the same cycle where the electrocardiosignal is located and the instant value of the R point of the electrocardiosignal; and the principal component analysis is performed on the PTT and the characteristic values to implement the dimension reduction processing on the data to be input into the first trained blood pressure calculation model and the second trained blood pressure calculation model, so that the time required for calculating the blood pressure value and the blood pressure error value may be reduced.

The determination module 402 is particularly configured to input the principal component factor matrix extracted by the extraction module 406 to the first trained blood pressure calculation model, and determine a diastolic blood pressure and a systolic blood pressure of a beat corresponding to the principal component factor matrix.

The determination module 402 is further particularly configured to input the principal component factor matrix extracted by the extraction module 406 to the second trained blood pressure calculation model, and determine a diastolic blood pressure error value and a systolic blood pressure error of a beat corresponding to the principal component factor matrix.

According to the embodiments of the present disclosure, the data input to the first blood pressure calculation model and the second blood pressure calculation model are the principal component factor matrix, i.e., the data input to the blood pressure calculation model is the data subjected to the dimension reduction processing, so that the time required for calculating the blood pressure value and the blood pressure error value is reduced, and the time required for obtaining the continuous blood pressure is reduced, thus the user experience is improved.

Further, the blood pressure measuring apparatus 40 further includes: a training module 407.

The training module 407 is configured to obtain the first trained blood pressure calculation model by training the Elman neural network.

The training module 407 is particularly configured to train the Elman neural network by taking a plurality of principal component factor matrixes acquired within a preset sampling period, and reference values of the diastolic blood pressures and reference values of the systolic blood pressures which are measured at the same beats as those for the respective principal component factor matrixes within the preset sampling period as training samples, so as to obtain the first trained blood pressure calculation model.

The principal component factor matrixes are obtained by performing differential processing and principal component analysis on the electrocardiosignals and the blood oxygen volume wave signals.

According to the embodiments of the present disclosure, the first trained blood pressure calculation model is trained by taking the plurality of principal component factor matrixes acquired within the preset sampling period, and the reference values of the diastolic blood pressures and the reference values of the systolic blood pressures which are measured at the same beats as those for the respective principal component factor matrixes as training samples, in order to obtain the beat-wise blood pressure values within the preset measurement period.

The training module 407 is further configured to obtain a second trained blood pressure calculation model by training the linear neural network.

According to an embodiment of the present disclosure, the linear neural network is the simplest neural network, and may be composed of one or more linear neurons. The linear neural network has high convergence speed and high precision. Thus, the second blood pressure calculation model obtained by training the linear neural network in this step is for the purpose of obtaining the error value of the diastolic blood pressure and the error value of the systolic blood pressure, which improve the precision of the determined error values of the diastolic blood pressure and the systolic blood pressure.

The training module 407 is further particularly configured to train the linear neural network by taking a plurality of principal component factor matrixes acquired within a preset sampling period and blood pressure error information corresponding to the respective principal component factor matrixes as training samples, to obtain the second trained blood pressure calculation model.

The blood pressure error information includes: diastolic blood pressure error information and systolic blood pressure error information, wherein the diastolic blood pressure error information is a difference between the diastolic blood pressure output in the training process of the Elman neural network and the reference value of the diastolic blood pressure measured at the same beat; and the systolic blood pressure error information is a difference between the systolic blood pressure output in the training process of the Elman neural network and the reference value of the systolic blood pressure measured at the same beat.

According to the embodiments of the present disclosure, the second blood pressure calculation model is trained by taking the respective principal component factor matrixes and the blood pressure error information corresponding to the principal component factor matrixes as training samples to obtain the second trained blood pressure calculation model, so as to correct the blood pressure information output by the first blood pressure calculation model, thereby obtaining more accurate blood pressure information.

An embodiment of the present disclosure provides another blood pressure measuring apparatus, which is configured to: acquire the electrocardiosignal and the blood oxygen volume wave signal of the target object within the preset measurement period; and then determine beat-wise blood pressure values of the target object within the preset measurement period by means of the first trained blood pressure calculation model based on the acquired electrocardiosignal and blood oxygen volume wave signal. That is, the blood pressure measuring apparatus may acquire a plurality of continuous diastolic blood pressures and a plurality of corresponding continuous systolic blood pressures within the preset measurement period based on the electrocardiosignal and the blood oxygen volume wave signal measured within the preset measurement period. For example, 60 diastolic blood pressures and the corresponding 60 systolic blood pressures, instead of only one diastolic blood pressure and one systolic blood pressure, are acquired within 1 minute of measurement period, so that the accuracy of measuring the blood pressure may be improved.

The advantages of the blood pressure measuring apparatus according to an embodiment of the present disclosure are described in detail in the description related to the electronic device described in any embodiment of the present disclosure above, and thus are not repeated herein.

An embodiment of the present disclosure provides a blood pressure measuring method. The blood pressure measuring method according to an embodiment of the present disclosure may be performed at the electronic device as shown in FIG. 1c or the blood pressure measuring apparatus as shown in FIG. 3 or the blood pressure measuring apparatus as shown in FIG. 4.

As shown in FIG. 2b, the blood pressure measuring method according to an embodiment of the present disclosure includes step S101 of acquiring an electrocardiographic signal and a blood oxygen volume wave signal of a target object within a preset measurement period.

According to an embodiment of the present disclosure, the electrocardiosignal is a bioelectric signal generated by the excitation of the cardiac muscle during the heart activity. In an embodiment of the present disclosure, the electrocardiographic signal may be recorded by an electrocardiograph machine.

For an embodiment of the present disclosure, the blood oxygen volume wave is used to represent the variation of blood oxygen concentration in blood per unit volume. According to an embodiment of the present disclosure, the blood oxygen volume wave signal of the target object may be continuously detected by the existing blood oxygen volume wave measuring method. The blood oxygen volume wave signal of the target subject is continuously detected, for example, by a photoplethysmography method.

According to an embodiment of the present disclosure, the preset measurement period may be set by the electronic device or the user, which is not limited in the embodiments of the present disclosure. For example, the preset measurement period may be 1 minute, 2 minutes, or the like.

According to an embodiment of the present disclosure, the way of acquiring the electrocardiosignal and the blood oxygen volume wave signal of the target object within the preset measurement period may comprise acquiring the electrocardiosignal and the blood oxygen volume wave signal of the target object within the preset measurement period in real time, or receiving the input electrocardiosignal and the blood oxygen volume wave signal of the target object measured within the preset measurement period, which is not limited by the embodiments of the present disclosure. In an embodiment of the present disclosure, the measurement periods of the electrocardiosignal and the blood oxygen volume wave signal are the same.

According to an embodiment of the present disclosure, the target object is a user who needs to measure the beat-wise blood pressure.

In step S102, beat-wise blood pressure values of the target object within the preset measurement period are determined based on the acquired electrocardiosignal and blood oxygen volume wave signal by means of a first trained blood pressure calculation model.

The blood pressure values may include a diastolic blood pressure and a systolic blood pressure.

According to an embodiment of the present disclosure, the determination of the beat-wise blood pressure values of the target object within the preset measurement period means that one diastolic blood pressure and one corresponding systolic blood pressure may be determined upon one beat of the heart or pulse within the preset measurement period.

For example, if the preset measurement period is 1 minute, and the target object's heart beats 60 times within 1 minute, 60 diastolic blood pressures and corresponding 60 systolic blood pressures of the target object are determined within 1 minute.

An embodiment of the present disclosure provides a blood pressure measuring method, which includes: acquiring the electrocardiosignal and the blood oxygen volume wave signal of the target object within the preset measurement period; and then determine the beat-wise blood pressure values of the target object within the preset measurement period by means of the first trained blood pressure calculation model based on the acquired electrocardiosignal and blood oxygen volume wave signal. That is, a plurality of continuous diastolic blood pressures and a plurality of corresponding continuous systolic blood pressures may be acquired within the preset measurement period based on the electrocardiosignal and the blood oxygen volume wave signal measured within the preset measurement period. For example, 60 diastolic blood pressures and the corresponding 60 systolic blood pressures, instead of only one diastolic blood pressure and one systolic blood pressure, are acquired within a measurement time of 1 minute, so that the accuracy of measuring the blood pressure may be improved.

The blood pressure measuring method of an embodiment of the present disclosure may also perform the steps as shown in FIG. 2a, in which step S102 is followed by step S203 and step S204, wherein the operations performed in step S201 and step S202 are the same as those performed in step S101 and step S102, and are thus not repeated herein.

In step S203, an error value corresponding to a diastolic blood pressure of each beat of the target object within the preset measurement period and an error value corresponding to a systolic blood pressure of each beat of the target object within the preset measurement period are determined based on the acquired electrocardiosignal and blood oxygen volume wave signal by means of a second trained blood pressure calculation model.

In step S204, based on the error value corresponding to the diastolic blood pressure of each beat of the target object within the preset measurement period, the diastolic blood pressure of the corresponding beat determined by means of the first trained blood pressure calculation model is corrected so as to determine the corrected beat-wise diastolic blood pressures of the target object within the preset measurement period; and based on the error value corresponding to the systolic blood pressure of each beat of the target object within the preset measurement period, the systolic blood pressure of the corresponding beat determined by means of the first trained blood pressure calculation model is corrected so as to determine the corrected beat-wise systolic blood pressures of the target object within the preset measurement period.

The blood pressure measurement method of an embodiment of the present disclosure may also perform steps A, B and C as shown in FIG. 2b.

In step A, a differential processing is performed on the acquired blood oxygen volume wave signal to obtain a plurality of characteristic values of the blood oxygen volume wave signal.

In step B, a pulse wave transmission time 'PTT' is determined based on a maximum of a first derivative of the blood oxygen volume wave signal in the same cycle where the electrocardiosignal is located and an instant value of an R point of the electrocardiosignal, wherein the R point of the electrocardiosignal signal is shown in FIG. 2c.

In step C, a principal component analysis processing is performed on the PTT and the plurality of characteristic values of the blood oxygen volume wave signal, and principal component factors that satisfy a preset condition are extracted to obtain a principal component factor matrix.

The blood pressure measuring method of an embodiment of the present disclosure may also perform step D as shown in FIG. 2b.

In step D, the principal component factor matrix is input to the first trained blood pressure calculation model to determine the diastolic blood pressure and the systolic blood pressure of the beat corresponding to the principal component factor matrix.

The blood pressure measuring method of an embodiment of the present disclosure may also perform step E as shown in FIG. 2b.

In step E, the principal component factor matrix is input to the second trained blood pressure calculation model to determine the error value corresponding to the diastolic blood pressure and the error value corresponding to the systolic blood pressure of the beat corresponding to the principal component factor matrix.

The blood pressure measurement method of an embodiment of the present disclosure may also perform step S110 as shown in FIG. 1d, in which the Elman neural network is trained to obtain the first trained blood pressure calculation model.

Particularly, step S110 may include: training the Elman neural network by taking a plurality of principal component factor matrixes acquired within a preset sampling period, and reference values of the diastolic blood pressures and reference values of the systolic blood pressures which are measured at the same beats as those for the respective principal component factor matrixes within the preset sampling period as training samples, so as to obtain the first trained blood pressure calculation model.

The blood pressure measurement method according to an embodiment of the present disclosure may also perform step S210 as shown in FIG. 2a, in which the linear neural network is trained to obtain the second trained blood pressure calculation model.

Specifically, step S210 may include: train the linear neural network by taking a plurality of principal component factor matrixes acquired within a preset sampling period and blood pressure error information corresponding to the respective principal component factor matrixes as training samples, so as to obtain the second trained blood pressure calculation model.

An embodiment of the present disclosure provides a computer-readable storage medium on which a computer program is stored, the computer program, which when executed by a processor, causes the processor to:

acquire an electrocardiosignal and a blood oxygen volume wave signal of a target object within a preset measurement period; and determine beat-wise blood pressure values of the target object within the preset measurement period by means of a first trained blood pressure calculation model based on the acquired electrocardiosignal and blood oxygen volume wave signal.

The blood pressure values include a diastolic blood pressure and a systolic blood pressure.

In another embodiment, the program, when executed by the processor, further causes the processor to, after the beat-wise blood pressure values of the target object within the preset measurement period are determined, determine an error value corresponding to a diastolic blood pressure of each beat of the target object within the preset measurement period and an error value corresponding to a systolic blood pressure of each beat of the target object within the preset measurement period by means of a second trained blood pressure calculation model based on the acquired electrocardiosignal and blood oxygen volume wave signal; and correct the diastolic blood pressure of the corresponding beat determined by means of the first trained blood pressure calculation model based on the error value corresponding to the diastolic blood pressure of each beat of the target object within the preset measurement period so as to determine the corrected beat-wise diastolic blood pressures of the target object within the preset measurement period; and correct the systolic blood pressure of the corresponding beat determined by means of the first trained blood pressure calculation model based on the error value corresponding to the systolic blood pressure of each beat of the target object within the preset measurement period so as to determine the corrected beat-wise systolic blood pressures of the target object within the preset measurement period.

In another embodiment, the program, when executed by the processor, further causes the processor to, before the beat-wise blood pressure values of the target object within the preset measurement period are determined based on the acquired electrocardiosignal and blood oxygen volume wave signal by means of the first trained blood pressure calculation model: perform a differential processing on the acquired blood oxygen volume wave signal to obtain a plurality of characteristic values of the blood oxygen volume wave signal;

determine a pulse wave transmission time 'PTT' based on a maximum of a first derivative of the blood oxygen volume wave signal in the same cycle where the electrocardiosignal is located and an instant value of an R point of the electrocardiosignal; and perform a principal component analysis processing on the PTT and the plurality of characteristic values of the blood oxygen volume wave signal, and extract principal component factors that satisfy a preset condition to obtain a principal component factor matrix.

In another embodiment, the program, when executed by the processor, further causes the processor to, determine the beat-wise blood pressure values of the target object within the preset measurement period by means of the first trained blood pressure calculation model based on the acquired electrocardiosignal and blood oxygen volume wave signal by:

inputting the principal component factor matrix to the first trained blood pressure calculation model to determine the diastolic blood pressure and the systolic blood pressure of the beat corresponding to the principal component factor matrix;

wherein the program, when executed by the processor, further causes the processor to determine the error value corresponding to the diastolic blood pressure of a beat of the target object within the preset measurement period and the error value corresponding to the systolic blood pressure of the beat of the target object within the preset measurement period by means of the second trained blood pressure calculation model based on the acquired electrocardiosignal and blood oxygen volume wave signal by:

inputting the principal component factor matrix to the second trained blood pressure calculation model to determine the error value corresponding to the diastolic blood pressure and the error value corresponding to the systolic blood pressure of the beat corresponding to the principal component factor matrix.

In another embodiment, the program, when executed by the processor, further causes the processor to, before the beat-wise blood pressure values of the target object within the preset measurement period are determined based on the acquired electrocardiosignal and blood oxygen volume wave signal by means of the first trained blood pressure calculation model:

train an Elman neural network to obtain the first trained blood pressure calculation model.

In another embodiment, the program, when executed by the processor, further causes the processor to train the Elman neural network to obtain the first trained blood pressure calculation model by:

training the Elman neural network by taking a plurality of principal component factor matrixes acquired within a preset sampling period, and reference values of the diastolic blood pressures and reference values of the systolic blood pressures which are measured at the same beats as those for the respective principal component factor matrixes within the preset sampling period as training samples, so as to obtain the first trained blood pressure calculation model, wherein the principal component factor matrixes are obtained by performing differential processing and principal component analysis on the electrocardiosignals and blood oxygen volume wave signals.

In another embodiment, the program, when executed by the processor, further causes the processor to, before the error value corresponding to the diastolic blood pressure of each beat of the target object within the preset measurement period and the error value corresponding to the systolic blood pressure of each beat of the target object within the preset measurement period are determined based on the acquired electrocardiosignal and blood oxygen volume wave signal by means of the second trained blood pressure calculation model:

train a linear neural network to obtain the second trained blood pressure calculation model.

In another embodiment, the program, when executed by the processor, further causes the processor to train the linear neural network to obtain the second trained blood pressure calculation model by:

training the linear neural network by taking a plurality of principal component factor matrixes acquired within a preset sampling period and blood pressure error information corresponding to the respective principal component factor matrixes as training samples, so as to obtain the second trained blood pressure calculation model;

wherein the blood pressure error information comprises: diastolic blood pressure error information and systolic blood pressure error information, wherein the diastolic blood pressure error information is a difference between the diastolic blood pressure output in the training process of the Elman neural network and the reference value of the diastolic blood pressure measured at the same beat; and the systolic blood pressure error information is a difference between the systolic blood pressure output in the training process of the Elman neural network and the reference value of the systolic blood pressure measured at the same beat.

An embodiment of the present disclosure provides a computer-readable storage medium on which a computer program is stored. The program, when executed by a processor, causes the processor to acquire an electrocardiosignal and a blood oxygen volume wave signal of a target object within a preset measurement period; and then determine beat-wise blood pressure values of the target object within the preset measurement period by means of a first trained blood pressure calculation model based on the acquired electrocardiosignal and blood oxygen volume wave signal. That is, it may acquire a plurality of continuous diastolic blood pressures and a plurality of corresponding continuous systolic blood pressures within the preset measurement period based on the electrocardiosignal and the blood oxygen volume wave signal measured within the preset measurement period. For example, 60 diastolic blood pressures and the corresponding 60 systolic blood pressures, instead of only one diastolic blood pressure and one systolic blood pressure, are acquired within a measurement time of 1 minute, so that the accuracy of measuring the blood pressure may be improved.

The description of the computer-readable storage medium according to an embodiment of the present disclosure is particularly described in any embodiment of the present disclosure. The implementation principles are similar, and thus are not repeated herein.

It should be understood that although the steps in the flowchart of the drawings are shown in an order as indicated by the arrows, those steps are not necessarily performed in the order as indicated by the arrows. The steps are not strictly limited to their current order, but may be performed in other orders, unless explicitly stated herein. Furthermore, at least a portion of the steps in the flowcharts of the drawings may include a plurality of sub-steps or stages, which are not necessarily performed at the same time, but may be performed at different times, and the order of execution thereof is not necessarily performed sequentially, and may be performed in turn or alternately with other steps or at least a portion of the sub-steps or stages of other steps.

The above description is only a part of embodiments of the present disclosure. It should be noted that the skilled in the art can also make some improvements and retouching without departing from the principle of the present disclosure, which should be considered as falling into the protection scope of the present disclosure.

I claim:

1. An electronic device, comprising:
a processor configured to:
train an Elman neural network to obtain a first trained blood pressure calculation model, comprising: training the Elman neural network by taking a plurality of principal component factor matrices acquired within a preset sampling period, and reference values of diastolic blood pressures and reference values of systolic blood pressures which are measured at the same beats as those for respective principal component factor matrices within the preset sampling period as training samples, so as to obtain the first trained blood pressure calculation model, wherein the principal component factor matrices are obtained by performing differential processing and principal component analysis on electrocardiosignals and blood oxygen volume wave signals;
acquire an electrocardiosignal and a blood oxygen volume wave signal of a target object within a preset measurement period; and
determine beat-wise blood pressure values of the target object within the preset measurement period using the first trained blood pressure calculation model based on the electrocardiosignal and blood oxygen volume wave signal of the target object acquired within the preset measurement period.

2. The electronic device of claim 1, wherein the beat-wise blood pressure values comprise a diastolic blood pressure and a systolic blood pressure, and
wherein the processor is further configured to, after the beat-wise blood pressure values of the target object within the preset measurement period are determined:
determine an error value corresponding to a diastolic blood pressure of each beat of the target object within the preset measurement period and an error value corresponding to a systolic blood pressure of each beat of the target object within the preset measurement period using a second trained blood pressure calculation model based on the acquired electrocardiosignal and blood oxygen volume wave signal; and
correct the diastolic blood pressure of the corresponding beat, determined of using the first trained blood pressure calculation model, based on the error value corresponding to the diastolic blood pressure of each beat of the target object within the preset measurement period so as to determine the corrected beat-wise diastolic blood pressures of the target object within the preset measurement period; and correct the systolic blood pressure of the corresponding beat, determined using the first trained blood pressure calculation model, based on the error value corresponding to the systolic blood pressure of each beat of the target object within the preset measurement period so as to determine the corrected beat-wise systolic blood pressures of the target object within the preset measurement period.

3. The electronic device of claim 2, wherein the processor is further configured to, before the beat-wise blood pressure values of the target object within the preset measurement period are determined based on the acquired electrocardiosignal and blood oxygen volume wave signal using the first trained blood pressure calculation model:
perform a differential processing on the acquired blood oxygen volume wave signal to obtain a plurality of characteristic values of the blood oxygen volume wave signal;
determine a pulse wave transmission time 'PTT' based on a maximum of a first derivative of the blood oxygen volume wave signal in the same cycle where the electrocardiosignal is located and an instant value of an R point of the electrocardiosignal; and
perform a principal component analysis processing on the PTT and the plurality of characteristic values of the blood oxygen volume wave signal, and extract principal component factors that satisfy a preset condition to obtain a principal component factor matrix.

4. The electronic device of claim 3, wherein the processor is further configured to determine the beat-wise blood pressure values of the target object within the preset measurement period using the first trained blood pressure calculation model based on the acquired electrocardiosignal and blood oxygen volume wave signal by:
inputting the principal component factor matrix to the first trained blood pressure calculation model to determine the diastolic blood pressure and the systolic blood pressure of the beat corresponding to the principal component factor matrix; and
wherein the processor is further configured to determine the error value corresponding to the diastolic blood pressure of a beat of the target object within the preset measurement period and the error value corresponding to the systolic blood pressure of the beat of the target object within the preset measurement period using the second trained blood pressure calculation model based on the acquired electrocardiosignal and blood oxygen volume wave signal by:
inputting the principal component factor matrix to the second trained blood pressure calculation model to determine the error value corresponding to the diastolic blood pressure and the error value corresponding to the systolic blood pressure of the beat corresponding to the principal component factor matrix.

5. The electronic device of claim 2, wherein the processor is further configured to, before the error value corresponding to the diastolic blood pressure of each beat of the target object within the preset measurement period and the error value corresponding to the systolic blood pressure of each beat of the target object within the preset measurement period are determined based on the acquired electrocardiosignal and blood oxygen volume wave signal using the second trained blood pressure calculation model:
train a linear neural network to obtain the second trained blood pressure calculation model.

6. The electronic device of claim 5, wherein the processor is further configured to train the linear neural network to obtain the second trained blood pressure calculation model by:
training the linear neural network by taking the plurality of principal component factor matrices acquired within the preset sampling period and blood pressure error information corresponding to the respective principal component factor matrices as training samples, so as to obtain the second trained blood pressure calculation model;

wherein the blood pressure error information comprises: diastolic blood pressure error information and systolic blood pressure error information, wherein the diastolic blood pressure error information is a difference between the diastolic blood pressure output in the training process of the Elman neural network and the reference value of the diastolic blood pressure measured at the same beat; and the systolic blood pressure error information is a difference between the systolic blood pressure output in the training process of the Elman neural network and the reference value of the systolic blood pressure measured at the same beat.

7. A blood pressure measuring method, comprising:

training an Elman neural network to obtain a first trained blood pressure calculation model, comprising: training the Elman neural network by taking a plurality of principal component factor matrices acquired within a preset sampling period, and reference values of diastolic blood pressures and reference values of systolic blood pressures which are measured at the same beats as those for the respective principal component factor matrices within the preset sampling period as training samples, so as to obtain the first trained blood pressure calculation model, wherein the principal component factor matrices are obtained by performing differential processing and principal component analysis on electrocardiosignals and blood oxygen volume wave signals;

acquiring an electrocardiosignal and a blood oxygen volume wave signal of a target object input within a preset measurement period; and determining beat-wise blood pressure values of the target object within the preset measurement period using the first trained blood pressure calculation model based on the electrocardiosignal and blood oxygen volume wave signal of the target object acquired within the preset measurement period.

8. The blood pressure measuring method of claim 7, wherein the beat-wise blood pressure values comprise a diastolic blood pressure and systolic blood pressure, and the blood pressure measuring method further comprises:

determining an error value corresponding to a diastolic blood pressure of each beat of the target object within the preset measurement period and an error value corresponding to a systolic blood pressure of each beat of the target object within the preset measurement period using a second trained blood pressure calculation model based on the acquired electrocardiosignal and blood oxygen volume wave signal;

correcting the diastolic blood pressure of the corresponding beat, determined using the first trained blood pressure calculation model, based on the determined error value corresponding to the diastolic blood pressure of each beat of the target object within the preset measurement period so as to determine the corrected beat-wise diastolic blood pressures of the target object within the preset measurement period; and correcting the systolic blood pressure of the corresponding beat, determined using the first trained blood pressure calculation model, based on the determined error value corresponding to the systolic blood pressure of each beat of the target object within the preset measurement period so as to determine the corrected beat-wise systolic blood pressures of the target object within the preset measurement period.

9. The blood pressure measuring method of claim 8, wherein before determining beat-wise blood pressure values of the target object within the preset measurement period using a first trained blood pressure calculation model based on the acquired electrocardiosignal and blood oxygen volume wave signal, the blood pressure measuring method further comprises:

performing a differential processing on the acquired blood oxygen volume wave signal to obtain a plurality of characteristic values of the blood oxygen volume wave signal;

determining a pulse wave transmission time 'PTT' based on a maximum of a first derivative of the blood oxygen volume wave signal in the same cycle where the electrocardiosignal is located and an instant value of an R point of the electrocardiosignal;

performing a principal component analysis processing on the PTT and the plurality of characteristic values of the blood oxygen volume wave signal; and extracting principal component factors that satisfy a preset condition to obtain a principal component factor matrix.

10. The blood pressure measuring method of claim 9, wherein determining beat-wise blood pressure values of the target object within the preset measurement period using a first trained blood pressure calculation model based on the acquired electrocardiosignal and blood oxygen volume wave signal comprises:

inputting the extracted principal component factor matrix to the first trained blood pressure calculation model to determine the diastolic blood pressure and the systolic blood pressure of the beat corresponding to the principal component factor matrix; and wherein determining an error value corresponding to a diastolic blood pressure of each beat of the target object within the preset measurement period and an error value corresponding to a systolic blood pressure of each beat of the target object within the preset measurement period using a second trained blood pressure calculation model based on the acquired electrocardiosignal and blood oxygen volume wave signal comprises:

inputting the extracted principal component factor matrix to the second trained blood pressure calculation model to determine the error value corresponding to the diastolic blood pressure and the error value corresponding to the systolic blood pressure of the beat corresponding to the principal component factor matrix.

11. The blood pressure measuring method of claim 8, further comprising:

training a linear neural network to obtain the second trained blood pressure calculation model.

12. The blood pressure measuring method of claim 11, wherein said training the linear neural network to obtain the second trained blood pressure calculation model comprises:

training the linear neural network by taking the plurality of principal component factor matrices acquired within the preset sampling period and blood pressure error information corresponding to the respective principal component factor matrixes as training samples, so as to obtain the second trained blood pressure calculation model;

wherein the blood pressure error information comprises: diastolic blood pressure error information and systolic blood pressure error information, wherein the diastolic blood pressure error information is a difference between the diastolic blood pressure output in the training process of the Elman neural network and the reference value of the diastolic blood pressure measured at the same beat; and the systolic blood pressure error information is a difference between the systolic blood pressure output in the training process of the Elman neural network and the reference value of the systolic blood pressure measured at the same beat.

13. A computer-readable storage medium on which a computer program is stored, wherein the computer program, when executed by a processor, causes the processor to:
   train an Elman neural network to obtain a first trained blood pressure calculation model, comprising: train the Elman neural network by taking a plurality of principal component factor matrices acquired within a preset sampling period, and reference values of diastolic blood pressures and reference values of systolic blood pressures which are measured at the same beats as those for the respective principal component factor matrices within the preset sampling period as training samples, so as to obtain the first trained blood pressure calculation model, wherein the principal component factor matrices are obtained by performing differential processing and principal component analysis on electrocardiosignals and blood oxygen volume wave signals;
   acquire an electrocardiosignal and a blood oxygen volume wave signal of a target object within a preset measurement period; and
   determine beat-wise blood pressure values of the target object within the preset measurement period using the first trained blood pressure calculation model based on the electrocardiosignal and blood oxygen volume wave signal of the target object acquired within the preset measurement period.

14. The computer-readable storage medium of claim 13, wherein the beat-wise blood pressure values comprise a diastolic blood pressure and a systolic blood pressure, and wherein the computer program, when executed by the processor, further causes the processor to:
   determine an error value corresponding to a diastolic blood pressure of each beat of the target object within the preset measurement period and an error value corresponding to a systolic blood pressure of each beat of the target object within the preset measurement period using a second trained blood pressure calculation model based on the acquired electrocardiosignal and blood oxygen volume wave signal;
   correct the diastolic blood pressure of the corresponding beat, determined using the first trained blood pressure calculation model, based on the error value corresponding to the diastolic blood pressure of each beat of the target object within the preset measurement period so as to determine the corrected beat-wise diastolic blood pressures of the target object within the preset measurement period; and
   correct the systolic blood pressure of the corresponding beat, determined using the first trained blood pressure calculation model, based on the error value corresponding to the systolic blood pressure of each beat of the target object within the preset measurement period so as to determine the corrected beat-wise systolic blood pressures of the target object within the preset measurement period.

15. The computer-readable storage medium of claim 14, wherein the computer program, when executed by the processor, further causes the processor to:
   perform a differential processing on the acquired blood oxygen volume wave signal to obtain a plurality of characteristic values of the blood oxygen volume wave signal;
   determine a pulse wave transmission time 'PTT' based on a maximum of a first derivative of the blood oxygen volume wave signal in the same cycle where the electrocardiosignal is located and an instant value of an R point of the electrocardiosignal; and
   perform a principal component analysis processing on the PTT and the plurality of characteristic values of the blood oxygen volume wave signal, and extract principal component factors that satisfy a preset condition to obtain a principal component factor matrix.

16. The computer-readable storage medium of claim 15, wherein the computer program, when executed by the processor, further causes the processor to:
   input the principal component factor matrix to the first trained blood pressure calculation model to determine the diastolic blood pressure and the systolic blood pressure of the beat corresponding to the principal component factor matrix; and
   input the principal component factor matrix to the second trained blood pressure calculation model to determine the error value corresponding to the diastolic blood pressure and the error value corresponding to the systolic blood pressure of the beat corresponding to the principal component factor matrix.

* * * * *